(12) United States Patent
Pitzer et al.

(10) Patent No.: US 8,536,764 B2
(45) Date of Patent: Sep. 17, 2013

(54) ARRANGEMENT OF A PIEZOACOUSTIC RESONATOR ON AN ACOUSTIC MIRROR OF A SUBSTRATE, METHOD FOR PRODUCING THE ARRANGEMENT AND USE OF THE ARRANGEMENT

(75) Inventors: Dana Pitzer, Unterschleissheim (DE); Matthias Schreiter, München (DE)

(73) Assignee: Siemens Aktiengesellschaft, Munich (DE)

( * ) Notice: Subject to any disclaimer, the term of this patent is extended or adjusted under 35 U.S.C. 154(b) by 339 days.

(21) Appl. No.: 12/997,094

(22) PCT Filed: Jun. 15, 2009

(86) PCT No.: PCT/EP2009/057341
§ 371 (c)(1),
(2), (4) Date: Dec. 9, 2010

(87) PCT Pub. No.: WO2009/153235
PCT Pub. Date: Dec. 23, 2009

(65) Prior Publication Data
US 2011/0089786 A1    Apr. 21, 2011

(30) Foreign Application Priority Data
Jun. 20, 2008  (DE) .......................... 10 2008 029 378

(51) Int. Cl.
*H01L 41/08*    (2006.01)
(52) U.S. Cl.
USPC .......................................... 310/326; 310/327
(58) Field of Classification Search
USPC .......................................... 310/320, 326, 327
See application file for complete search history.

(56) References Cited

U.S. PATENT DOCUMENTS

| | | | |
|---|---|---|---|
| 6,927,649 B2 * | 8/2005 | Metzger et al. | 333/133 |
| 7,310,861 B2 | 12/2007 | Aigner et al. | 29/25.35 |
| 7,468,608 B2 | 12/2008 | Feucht et al. | 324/633 |
| 7,479,851 B2 | 1/2009 | Aigner et al. | 333/189 |

(Continued)

FOREIGN PATENT DOCUMENTS

| | | |
|---|---|---|
| DE | 102004058064 A1 | 6/2006 |
| JP | 2004187204 A | 7/2004 |

(Continued)

OTHER PUBLICATIONS

International PCT Search Report and Written Opinion, PCT/EP2009/057341, 13 pages.

*Primary Examiner* — Thomas Dougherty
(74) *Attorney, Agent, or Firm* — King & Spalding L.L.P.

(57) ABSTRACT

In an arrangement of at least one piezoacoustic resonator on a substrate surface, the resonator has an piezoelectric layer, an electrode and a further electrode arranged such that activation of the electrodes leads to a resonance oscillation, the substrate surface is formed by an acoustic mirror integrated in the substrate for acoustically insulating substrate and resonator, and with a resonance frequency evaluation device being connected to the electrodes by tracks being routed through a mirror opening. The acoustic mirror has a Bragg reflector having λ/4-thick layers of different acoustic impedance. The topmost layer is made of silicon dioxide acting as an insulation layer in the mirror opening for electrically insulating the conductor track and the electrically conductive Bragg reflector layers. The arrangement is used as a physical transducer of a device for detecting a substance of a fluid, in particular of a fluid in the form of a liquid (biosensor).

19 Claims, 2 Drawing Sheets

(56) References Cited

U.S. PATENT DOCUMENTS

| | | |
|---|---|---|
| 7,737,804 B2 | 6/2010 | Bouche et al. ............... 333/187 |
| 2004/0201305 A1 | 10/2004 | Aigner et al. ............... 310/311 |
| 2005/0167854 A1* | 8/2005 | Tikka et al. ................. 257/787 |
| 2006/0125489 A1 | 6/2006 | Feucht et al. ............... 324/633 |
| 2006/0202779 A1 | 9/2006 | Fazzio et al. ............... 333/197 |
| 2006/0232361 A1 | 10/2006 | Wang et al. ................. 333/133 |
| 2007/0007851 A1 | 1/2007 | Loebl et al. ................. 310/313 |
| 2007/0052327 A1* | 3/2007 | Vilander ...................... 310/343 |
| 2007/0152777 A1 | 7/2007 | Bouche et al. .............. 333/187 |
| 2007/0210349 A1* | 9/2007 | Lu et al. ....................... 257/252 |
| 2008/0048802 A1 | 2/2008 | Aigner et al. ............... 333/189 |
| 2008/0197430 A1 | 8/2008 | Aigner et al. ............... 257/414 |

FOREIGN PATENT DOCUMENTS

| | | |
|---|---|---|
| JP | 2005505178 A | 2/2005 |
| JP | 2005533265 A | 11/2005 |
| JP | 2007074727 A | 3/2007 |
| JP | 2007508539 A | 4/2007 |
| JP | 2009-194915 A * | 8/2009 |
| WO | 2004/017063 | 2/2004 |

* cited by examiner

ARRANGEMENT OF A PIEZOACOUSTIC RESONATOR ON AN ACOUSTIC MIRROR OF A SUBSTRATE, METHOD FOR PRODUCING THE ARRANGEMENT AND USE OF THE ARRANGEMENT

CROSS-REFERENCE TO RELATED APPLICATIONS

This application is a U.S. National Stage Application of International Application No. PCT/EP2009/057341 filed Jun. 15, 2009, which designates the United States of America, and claims priority to DE Application No. 10 2008 029 378.4 filed Jun. 20, 2008. The contents of which are hereby incorporated by reference in their entirety.

TECHNICAL FIELD

The invention relates to an arrangement of at least one piezoacoustic resonator on a surface of a substrate, wherein the resonator has at least one piezoelectric layer, an electrode and at least one further electrode which are arranged in relation to one another in such a way that a specific electrical activation of the electrodes leads to a resonance oscillation of the resonator at a resonance frequency, the surface of the substrate is formed by an acoustic mirror integrated in the substrate for the purpose of acoustically insulating the substrate and the resonator from each other, and at least one evaluation device is provided for the purpose of determining the resonance frequency of the resonator. A method for producing the arrangement and a use of the arrangement are also disclosed.

BACKGROUND

The piezoacoustic resonator is a piezoacoustic thin-film resonator (Film Bulk Acoustic resonator or FBAR), for example. A thin-film resonator of this type is described in WO 2004/017063 A2, for example. The thin-film resonator consists, for example, of two electrode layers and a piezoelectric layer arranged between the electrode layers in the form of a piezoceramic layer. The piezoceramic layer is a polycrystalline layer made up of zinc oxide monocrystals. The electrode layers are made of platinum, for example. The electrode layers and the piezoceramic layer are arranged in relation to one another in such a way that an electrical activation of the electrode layers by means of an electrical alternating field leads to an oscillation of the resonator. Activating the arrangement by means of a specific electrical alternating field results in a resonance oscillation at a specific resonance frequency. The resonance frequency of the oscillation is dependent inter alia on the layer thicknesses of the layers. Owing to an orientation of the zinc oxide monocrystals the thin-film resonator can be excited into longitudinal thickness mode oscillations and shear thickness mode oscillations.

In order to produce the layers of the thin-film resonator on the substrate, for example a silicon substrate, a vapor deposition method (deposition from the gas phase) is performed. An evaluation device is integrated in the substrate for the purpose of determining the resonance frequency. In this background art it is not disclosed how the evaluation device is brought into electrical contact with the electrode layers of the thin-film resonator.

SUMMARY

According to various embodiments, the electrodes of a piezoacoustic resonator are brought into electrical contact in a space-saving and reliable manner so that the resonance frequency of the resonator can be determined.

According to an embodiment, in an arrangement of at least one piezoacoustic resonator on a substrate surface of a substrate, —the resonator has at least one piezoelectric layer, an electrode and at least one further electrode which are arranged in relation to one another in such a way that a specific electrical activation of the electrodes leads to a resonance oscillation of the resonator at a resonance frequency, —the surface of the substrate is formed by an acoustic mirror integrated in the substrate for the purpose of acoustically insulating the substrate and the resonator from each other, and—at least one evaluation device is provided for the purpose of determining the resonance frequency of the resonator, —the evaluation device and at least one of the electrodes are connected to each other in an electrically conductive manner by way of an electric conductor track, and—the electric conductor track is routed through a mirror opening of the acoustic mirror.

According to a further embodiment, a lateral edge of the mirror opening of the acoustic mirror may have an electrical opening insulation layer comprising opening insulation material on which the electric conductor track is applied. According to a further embodiment, the evaluation device may have a readout circuit integrated in the substrate which is connected to the electrode in an electrically conductive manner by way of the electric conductor track. According to a further embodiment, the resonator may be a thin-film resonator. According to a further embodiment, one of the electrodes may have an electrode layer applied directly on the acoustic mirror. According to a further embodiment, the further electrode may have a further electrode layer which is applied on the piezoelectric layer. According to a further embodiment, the further electrode layer may be applied on the piezoelectric layer in such a way that the electrode layer, the further electrode layer and the piezoelectric layer form a resonator layer stack in which the piezoelectric layer is arranged between the electrode layers. According to a further embodiment, the acoustic mirror may have a mirror layer stack in which layers having lower acoustic impedance and higher acoustic impedance compared with one another are stacked alternately one on top of another, each of the layers having a layer thickness corresponding to approximately a quarter of a resonance wavelength of the resonance oscillation of the resonator. According to a further embodiment, the layers having lower acoustic impedance can be made of silicon dioxide. According to a further embodiment, the layers having higher acoustic impedance can be made of elementary tungsten. According to a further embodiment, the topmost layer of the mirror layer stack forming the surface of the substrate may have an electric mirror insulation layer comprising electric mirror insulation material and the mirror insulation material and the opening insulation material can be essentially identical. According to a further embodiment, a layer thickness of the mirror insulation layer and the layer thickness of the opening insulation layer can be essentially identical. According to a further embodiment, the mirror insulation layer and the opening insulation layer may form a cohesive overall insulation layer. According to a further embodiment, the opening insulation material and the mirror insulation material may include silicon dioxide.

According to another embodiment, a method for producing an arrangement as described above may comprise the following method steps of: a) providing a substrate with an acoustic mirror forming the substrate surface and a mirror opening present in the mirror via which a readout circuit of the evaluation device can be connected in an electrically conductive manner, and b) arranging the electric conductor track in the mirror opening in such a way that the readout circuit and the electric conductor track are connected in an electrically conductive manner.

According to a further embodiment of the method, the following further method steps can be performed in order to provide the substrate: a') providing a substrate with a readout circuit integrated in the substrate, a") mounting the acoustic mirror on the substrate over the readout circuit in such a way that the acoustic mirror forms the surface of the substrate, and a''') creating the mirror opening in the acoustic mirror in such a way that the readout circuit is made accessible. According to a further embodiment of the method, an acoustic mirror having a mirror layer stack can be used which has layers stacked alternately one on top of another, which layers have lower or higher acoustic impedances compared with one another and each of which has a layer thickness corresponding to approximately a quarter of a resonance wavelength of the resonance oscillation of the resulting resonator. According to a further embodiment of the method, the opening insulation layer can be applied after the mirror opening is created and the mirror insulation layer is applied during the application of the opening insulation layer in such a way that the mirror insulation layer forms the surface of the substrate. According to a further embodiment of the method, after the mirror insulation layer is applied the resonator can be mounted onto the surface of the substrate formed by the mirror insulation layer.

According to yet another embodiment, an arrangement as described above can be used as a physical transducer of a device for detecting a substance of a fluid.

BRIEF DESCRIPTION OF THE DRAWINGS

The invention is described in more detail below with reference to an exemplary embodiment and the associated figures. The figures are schematic and do not constitute true-to-scale representations.

DETAILED DESCRIPTION

Figure 1:
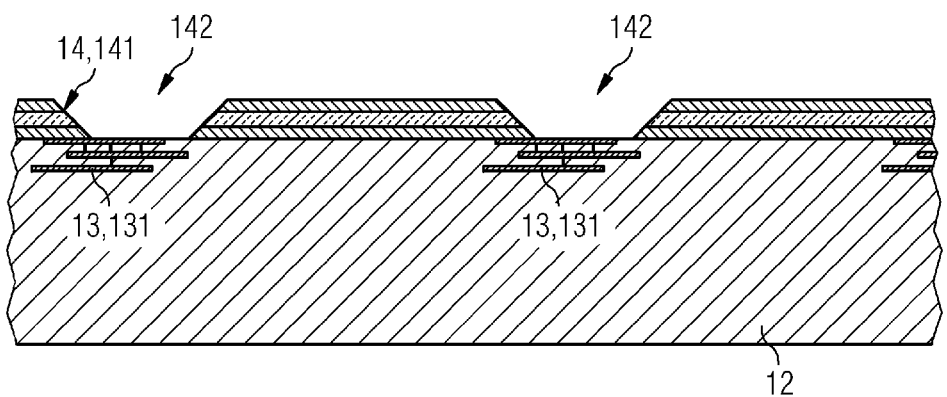
FIGS. 1 to 3 each show in lateral cross-section a detail of a development stage passed through during the method for producing the arrangement of a piezoacoustic resonator on a surface of a substrate.
Figure 2:
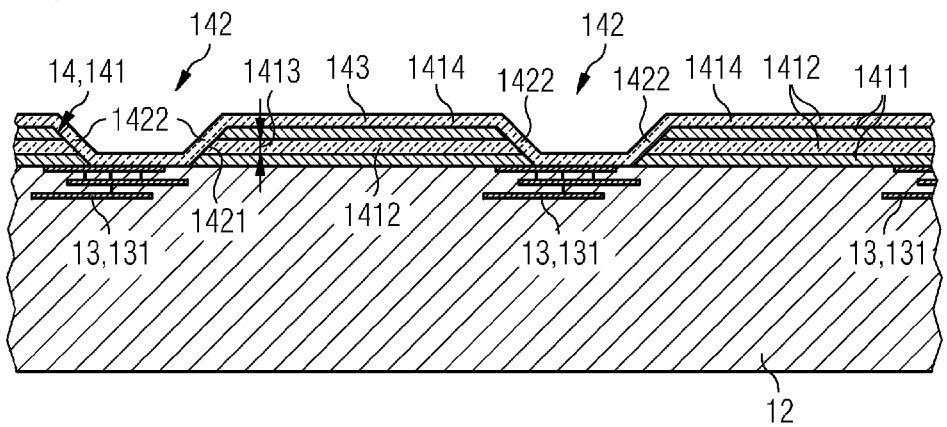
Figure 3:
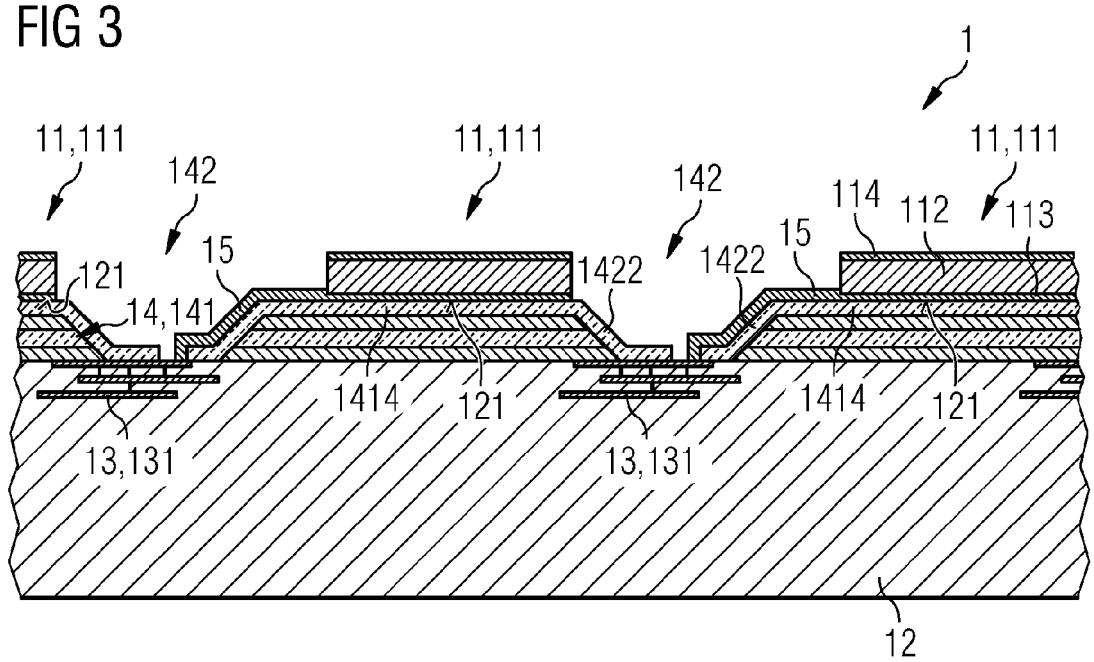

In order to achieve this object, an arrangement of at least one piezoacoustic resonator on a surface of a substrate is disclosed, wherein the resonator has at least one piezoelectric layer, an electrode and at least one further electrode which are arranged in relation to one another in such a way that a specific electrical activation of the electrode leads to a resonance oscillation of the resonator at a resonance frequency, wherein the surface of the substrate is formed by an acoustic mirror integrated in the substrate for the purpose of acoustically insulating the substrate and the resonator from each other, and wherein at least one evaluation device is provided for the purpose of determining the resonance frequency of the resonator. The arrangement is characterized in that the evaluation device and at least one of the electrodes are connected to each other in an electrically conductive manner by way of an electric conductor track and in that the electric conductor track is routed through a mirror opening of the acoustic mirror. The electric conductor track serves as a signal or ground line of the piezoacoustic resonator.

Also disclosed in order to achieve the object is a method for producing the arrangement, comprising the following method steps of:
a) providing a substrate with an acoustic mirror forming the substrate surface and a mirror opening present in the mirror via which a readout circuit of the evaluation device can be connected in an electrically conductive manner, and
b) arranging the electric conductor track in the mirror opening in such a way that the readout circuit and the electric conductor track are connected in an electrically conductive manner.

With regard to the method, the following further method steps in particular are performed for providing the substrate: a') providing a substrate with a readout circuit integrated in the substrate, a") mounting the acoustic mirror on the substrate over the readout circuit in such a way that the acoustic mirror forms the surface of the substrate, and a''') creating the mirror opening in the acoustic mirror in such a way that the readout circuit is made accessible. In this case the piezoacoustic resonator is preferably arranged on the acoustic mirror before the mirror opening is created.

Preferably an acoustic mirror comprising a mirror layer stack is used which has layers stacked alternately one on top of another, which layers have different acoustic impedances compared with one another and each of which has a layer thickness corresponding to approximately a quarter of a resonance wavelength $\lambda$ of a resonance oscillation of the resulting resonator. In order to deposit the layers, use is preferably made of a vapor deposition method, for example a chemical vapor deposition (CVD) method or a physical vapor deposition (PVD) method. The result is an acoustic mirror in the form of a Bragg reflector having $\lambda/4$-thick layers. In connection with silicon substrates, a layer sequence consisting of vertically stacked alternating layers of silicon dioxide and tungsten has proved particularly suitable.

In a special embodiment a lateral border (edge) of the mirror opening of the acoustic mirror has an electrical opening insulation layer comprising opening insulation material on which the electric conductor track is applied.

According to a special embodiment the topmost layer of the mirror layer stack forming the substrate surface has an electrical mirror insulation layer comprising electrical mirror insulation material. The mirror insulation material and the opening insulation material are essentially identical. This means that the mirror insulation layer, like the opening insulation layer, is made of silicon dioxide. In particular a layer thickness of the mirror insulation layer and the layer thickness of the opening insulation layer are essentially identical. Preferably the layer thickness is equal to approximately a quarter of the resonance wavelength $\lambda$ of the resonance oscillation of the resulting resonator.

According to a special embodiment the mirror insulation layer and the opening insulation layer form a cohesive overall insulation layer. Toward that end, in particular the opening insulation layer in the mirror opening is applied after the creation of the mirror opening, and the mirror insulation layer is applied during the application of the opening insulation layer in such a way that the mirror insulation layer forms the surface of the substrate. The insulation layers are produced in a single method step. It is, however, also possible in principle to produce the insulation layers sequentially and also from different insulation materials.

After the mirror insulation layer has been applied the resonator is mounted onto the surface of the substrate formed by the mirror insulation layer.

According to a special embodiment the resonator is a thin-film resonator. The electrodes are electrode layers. The electrode layers and the piezoelectric layer can be arranged arbitrarily in relation to one another. Preferably, however, the thin-film resonator comprises a resonator layer stack. In this case one of the electrodes has an electrode layer mounted on the acoustic mirror. The piezoelectric layer is applied over this. A further electrode has a further electrode layer applied directly on the piezoelectric layer. This results in a resonator layer stack in which a piezoelectric layer of the resonator is arranged between the electrode layers.

Preferably the piezoelectric layer is a polycrystalline layer consisting of zinc oxide or aluminum nitride. Given suitable orientation of the polar C-axes of the corresponding monocrystals it is possible to excite the piezoacoustic resonator into thickness shear mode oscillations.

The arrangement may be used as a physical transducer of a device for detecting a substance of a fluid. In this case use is made of the effect that by population of a resonator surface of the resonator a mass of the resonator increases and consequently the resonance frequency of the thin-film resonator decreases. Owing to the shear thickness mode oscillations it is possible to analyze a fluid in the form of a liquid with the aid of the present arrangement.

The following advantages of the various embodiments should be emphasized:

With the aid of various embodiments it is possible to build a space-saving layout of the arrangement consisting of a piezoacoustic resonator on a substrate.

In particular the use of an overall insulation layer which is composed of the topmost silicon dioxide layer of the mirror layer stack of the acoustic mirror and the opening insulation layer leads to a reliable electrical insulation of the electric conductor track from metallic mirror layers (tungsten mirror layers).

The layer thickness of λ/4 of the overall insulation layer that has been chosen with regard to the acoustic mirror simultaneously leads to a good capacitive decoupling of the electric conductor track and the acoustic mirror from each other. In the case of an overall insulation layer made of $SiO_2$, a layer thickness of the overall insulation layer of more than 1 μm is produced at a resonance frequency of less than 1 GHz, and hence an efficient electrical insulation is achieved.

Additional insulation layers are not necessary. This results in relatively low manufacturing costs.

The use of the topmost mirror layer as an insulation layer leads to a partial planarization of the structure of the acoustic mirror, which is advantageous for subsequent photolithographic processes that are possibly necessary in the construction of the resonator.

According to the exemplary embodiment the arrangement 1 has a resonator array consisting of three piezoacoustic resonators 11, each of which is disposed on a substrate surface 121 of a substrate 12. The piezoacoustic resonators are piezoacoustic thin-film resonators. These resonators consist of a resonator layer stack 11 having an electrode or electrode layer 113, a further electrode or further electrode layer 114, and a piezoelectric layer 112 arranged between the electrode layers. The piezoelectric layer is a polycrystalline ceramic layer of zinc oxide (zinc oxide film). The polar C-axes of the zinc oxide monocrystals of the zinc oxide film are tilted toward the substrate surface. This enables the resonator to be excited by electrical activation of the electrode layers not only to longitudinal thickness mode oscillations, but also to shear thickness mode oscillations. A layer thickness of the zinc oxide film is equal to approximately 0.5 μm. The electrode layers are made of platinum. The top electrode layer is approximately 100 nm thick and the bottom electrode layer 890 nm thick. A lateral extension of the thin-film resonator is equal to approximately 200 μm.

The substrate surface 121 of the substrate 12 is formed by an acoustic mirror 14 integrated in the substrate for the purpose of acoustically insulating the substrate and the resonator from each other. The acoustic mirror comprises a mirror layer stack 141. Said mirror layer stack constitutes a Bragg reflector in which layers having lower acoustic impedance 1411 and layers having higher acoustic impedance 1412 are stacked one on top of another. The layers having lower acoustic impedance are made of silicon dioxide. The layers having higher acoustic impedance are made of tungsten. The layer thicknesses of these layers of different acoustic impedance are equal to approximately a quarter of a resonance wavelength of the resonance oscillation of the resonator.

An evaluation device 13 is integrated in the substrate for the purpose of determining the resonance frequency of the resonator. The evaluation device possesses a readout circuit 131. Said readout circuit is connected to at least one of the electrodes in an electrically conductive manner. Toward that end an electric conductor track 15 is routed through mirror openings 142. The conductor track is made of aluminum. A lateral border (edge) 1421 of the mirror opening possesses an opening insulation layer 1422 for the purpose of electrically isolating the electric conductor track 15 and the electrically conductive tungsten layers 1411. The opening insulation layer is made of silicon dioxide.

The topmost layer of the mirror layer stack forms a mirror insulation layer 1414. Said mirror insulation layer and the opening insulation layer together form the overall insulation layer 143. The mirror insulation layer forms the surface of the substrate. The electrode layers of the thin-film resonators are applied directly onto the mirror insulation layer.

In order to produce the arrangement, the following method steps are performed: a) providing a substrate made of silicon with an acoustic mirror 14 forming the substrate surface 121 and a mirror opening 142 present in the mirror via which a readout circuit of the evaluation device integrated in the substrate can be connected in an electrically conductive manner, and b) arranging the electric conductor track in the mirror opening in such a way that the readout circuit and the electric conductor track are connected to each other in an electrically conductive manner.

In order to provide the substrate, the following further method steps are performed: a') providing the substrate with a readout circuit integrated in the substrate, a'') mounting the acoustic mirror on the substrate over the readout circuit in such a way that the acoustic mirror forms the surface of the substrate, and a''') creating the mirror opening in the acoustic mirror in such a way that the readout circuit is made accessible.

In order to produce the acoustic mirror, the individual layers of different acoustic impedance are applied by way of a vapor deposition method. In order to create the mirror openings, the mirror layer stack is first mounted and thereafter material of the mirror layer stack is removed again at the points under which the readout circuits are located.

Next, using a vapor deposition method, the overall insulation layer made of silicone dioxide, consisting of the opening insulation layer and the mirror insulation layer, is applied. This happens in a single method step. The overall insulation layer fulfills two functions: As a constituent part of the acoustic mirror the overall insulation layer contributes toward the acoustic insulation of the resonator and the substrate from each other. In addition it also acts as an electrical insulator.

Following this, the resonators are applied. This is effected in a known manner through deposition of the corresponding layers from the gas phase.

Next, an opening is created in the region of the opening insulation layer. One of the electrode layers of the resonator and the respective readout circuit are brought into electrical contact through said opening.

The arrangement may be used as a physical transducer of a device for detecting a substance of a fluid. Owing to the possibility of exciting the resonator not only to longitudinal thickness mode oscillations, but also to shear thickness mode oscillations, the arrangement is suitable for use in a fluid in the form of a liquid.

What is claimed is:

1. An arrangement of at least one piezoacoustic resonator on a substrate surface of a substrate, wherein
    the resonator has at least one piezoelectric layer, an electrode and at least one further electrode which are arranged in relation to one another in such a way that a specific electrical activation of the electrodes leads to a resonance oscillation of the resonator at a resonance frequency,
    the surface of the substrate is formed by an acoustic mirror integrated in the substrate for the purpose of acoustically insulating the substrate and the resonator from each other,
    at least one evaluation device is integrated in the substrate for determining the resonance frequency of the resonator,
    the evaluation device and at least one of the electrodes are connected to each other in an electrically conductive manner by way of an electric conductor track on the acoustic mirror, wherein
    the electric conductor track is routed through a mirror opening of the acoustic mirror; and wherein a lateral edge of the mirror opening of the acoustic mirror has an electrical opening insulation layer comprising opening insulation material on which the electric conductor track is applied.

2. The arrangement according to claim 1, wherein the evaluation device has a readout circuit integrated in the substrate which is connected to the electrode in an electrically conductive manner by way of the electric conductor track.

3. The arrangement according to claim 1, wherein the resonator is a thin-film resonator.

4. The arrangement according to claim 1, wherein one of the electrodes has an electrode layer applied directly on the acoustic mirror.

5. The arrangement according to claim 1, wherein the further electrode has a further electrode layer which is applied on the piezoelectric layer.

6. The arrangement according to claim 5, wherein the further electrode layer is applied on the piezoelectric layer in such a way that the electrode layer, the further electrode layer and the piezoelectric layer form a resonator layer stack in which the piezoelectric layer is arranged between the electrode layers.

7. The arrangement according to claim 1, wherein the acoustic mirror has a mirror layer stack in which layers having lower acoustic impedance and higher acoustic impedance compared with one another are stacked alternately one on top of another, each of the layers having a layer thickness corresponding to approximately a quarter of a resonance wavelength of the resonance oscillation of the resonator.

8. The arrangement according to claim 7, wherein the layers having lower acoustic impedance are made of silicon dioxide.

9. The arrangement according to claim 7, wherein the layers having higher acoustic impedance are made of elementary tungsten.

10. The arrangement according to claim 7, wherein the topmost layer of the mirror layer stack forming the surface of the substrate has an electric mirror insulation layer comprising electric mirror insulation material and the mirror insulation material and the opening insulation material are essentially identical.

11. The arrangement according to claim 10, wherein a layer thickness of the mirror insulation layer and the layer thickness of the opening insulation layer are essentially identical.

12. The arrangement according to claim 11, wherein the mirror insulation layer and the opening insulation layer form a cohesive overall insulation layer.

13. The arrangement according to claim 12, wherein the opening insulation material and the mirror insulation material include silicon dioxide.

14. A method for producing an arrangement of at least one piezoacoustic resonator on a substrate surface of a substrate, comprising:
    providing a substrate with an acoustic mirror forming a substrate surface and with a mirror opening in a mirror via which a readout circuit of an evaluation device integrated in the substrate can be connected in an electrically conductive manner,
    arranging an electric conductor track on the mirror and in the mirror opening in such a way that the readout circuit and the electric conductor track are connected in an electrically conductive manner; and
    providing a lateral edge of the mirror opening of the acoustic mirror with an electrical opening insulation layer comprising opening insulation material on which the electric conductor track is applied.

15. The method according to claim 14, wherein the following further method steps are performed in order to provide the substrate:
    a') providing a substrate with a readout circuit integrated in the substrate,
    a") mounting the acoustic mirror on the substrate over the readout circuit in such a way that the acoustic mirror forms the surface of the substrate, and
    a''') creating the mirror opening in the acoustic mirror in such a way that the readout circuit is made accessible.

16. The method according to claim 14, wherein an acoustic mirror having a mirror layer stack is used which has layers stacked alternately one on top of another, which layers have lower or higher acoustic impedances compared with one another and each of which has a layer thickness corresponding to approximately a quarter of a resonance wavelength of the resonance oscillation of the resulting resonator.

17. The method according to claim 14, wherein the opening insulation layer is applied after the mirror opening is created and the mirror insulation layer is applied during the application of the opening insulation layer in such a way that the mirror insulation layer forms the surface of the substrate.

18. The method according to claim 17, wherein after the mirror insulation layer is applied the resonator is mounted onto the surface of the substrate formed by the mirror insulation layer.

19. A method for using of an arrangement of at least one piezoacoustic resonator on a substrate surface of a substrate according to claim 1, comprising using the at least one piezoacoustic resonator on a substrate surface of a substrate as a physical transducer of a device for detecting a substance of a fluid.

* * * * *